United States Patent [19]

Zecher et al.

[11] 4,281,140

[45] Jul. 28, 1981

[54] PROCESS FOR THE PREPARATION OF HYDANTOINS

[75] Inventors: Wilfried Zecher; Rudolf Merten, both of Leverkusen, Fed. Rep. of Germany

[73] Assignee: Bayer Aktiengesellschaft, Leverkusen, Fed. Rep. of Germany

[21] Appl. No.: 61,061

[22] Filed: Jul. 26, 1979

Related U.S. Application Data

[62] Division of Ser. No. 854,111, Nov. 23, 1977, Pat. No. 4,182,812.

[30] Foreign Application Priority Data

Apr. 1, 1977 [DE] Fed. Rep. of Germany ....... 2714655

[51] Int. Cl.³ .......................................... C07D 233/64
[52] U.S. Cl. ................................................... 548/313
[58] Field of Search ........................................ 548/313

[56] References Cited

U.S. PATENT DOCUMENTS 4,089,860  5/1978  Merten et al. ....................... 548/310

*Primary Examiner*—Henry R. Jiles
*Assistant Examiner*—Jane T. Fan

*Attorney, Agent, or Firm*—Connolly and Hutz

[57] ABSTRACT

Hydantoins are prepared by reacting a monoisocyanate or a monoisothiocyanate with an unsaturated diamide at 0°–450° C. said diamide being a compound of the formula

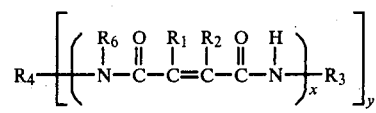

wherein $R_1$, $R_2$, $R_3$, $R_4$ and $R_6$ may be the same or different and each is selected from the group consisting of hydrogen, alkyl of 1–20 carbon atoms, alkenyl of 1–20 carbon atoms, aryl of 4–20 carbon atoms and aralkyl of 7–20 carbon atoms, and $R_4$ and $R_6$ together are additionally together a heterocyclic having 3–7 carbon atoms wherein the nitrogen heteroatom is bonded to both $R_3$ and $R_6$, and $R_1$ and $R_2$ are also additionally halogen, and x and y each are integer from 1 to 3, with the proviso that at least one of x and y is 1.

4 Claims, No Drawings

PROCESS FOR THE PREPARATION OF HYDANTOINS

This application is a division of application Ser. No. 854,111 filed Nov. 23, 1977, now U.S. Pat. No. 4,182,812.

It is already known that hydantoins are obtained when α-amino-carboxylic acid esters are reacted with isocyanates (Am. Chem. J. 45, 383). Another method of preparation is the reaction of α-aminonitriles with isocyanates, followed by saponification of the resulting imino compounds to form hydantoins.

While monomolecular hydantoins have interesting properties for the pharmaceutical field and the protection of plants, high molecular weight hydantoins have in recent years been introduced into the technical industry as temperature-resistant synthetic resins, particularly for the electrical insulation field (French Pat. No. 1,484,694=British Pat. No. 1,106,915).

It has now been found that hydantoins are obtained in high yields by reacting organic isocyanates with unsaturated diamides of the following general formula:

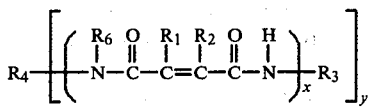

wherein
$R_1$, $R_2$, $R_3$, $R_4$ and $R6$ may be the same or different and represent hydrogen, an aliphatic, aliphatic-aromatic or aromatic radical, and
$R_1$ and $R_2$ may additionally represent halogen, and
x and y represent integers of from 1 to 3, preferably 1 or 2, at least x or y may be 1,
at temperatures of from 0° to 450° C., preferably from 50° to 250° C.

The course of the reaction is surprising since diamides of this constitution would have been expected to be cyclised to imides with liberation of amine, followed by further reaction with the isocyanate to form secondary products. The yields obtained from the reaction according to the invention are so high that even the production of polymeric products is possible. In contrast to the known processes for the preparation of hydantoins, this process is not accompanied by the liberation of any decomposition products such as water, alcohols or carbon dioxide which could lead to undesired side reactions, chain breaking or the formation of bubbles in the polymers.

The unsaturated diamines used as starting materials according to the invention may be obtained, for example, from the acid halides of the unsaturated amic acids or from unsaturated amido acids and isocyanates. They can be also prepared from the components in the reaction medium. It is preferred to use compounds of the following general formula:

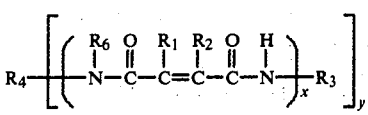

wherein
$R_1$, $R_2$, $R_3$, $R_4$ and $R_6$ may be the same or different and represent hydrogen, an aliphatic radical having from 1 to 20 C-atoms, an aliphatic-aromatic radical having from 7 to 20 C-atoms or an aromatic radical having from 4 to 20, preferably 6–16, C-atoms, and
$R_1$ and $R_2$ may additionally represent a halogen such as fluorine, chlorine or bromine, and
x and y have the same meaning as indicated above.

The groups $R_1$ and $R_2$ may be derived preferably from, for example, hydrogen, fluorine, chlorine, bromine, methane, ethane, hexane, cyclohexane, propene, toluene or benzene, or together they may form a ring with up to 8 carbon atoms. The groups $R_3$, $R_4$ and $R_6$ may be derived, for example, from hydrogen, methane, ethane, n-, iso- or tert.-butane, hexane, eicosane, propene, butane, cyclohexane, benzene, naphthalene, diphenylmethane, diphenylether, diphenylsulphone, α- or nuclear-substituted toluene, xylene, polyethers, polyesters, polyureas and polyurethanes, and they may be substituted one or more times, e.g. with halogen or with $C_1$–$C_{10}$ alkyl groups, carboxylic acid groups, hydroxyl groups or amino groups. $R_4$ and $R_6$ may also together form a heterocyclic group with 3 to 7 carbon atoms which may contain hetero atoms in addition to the nitrogen atom to which both groups are attached, e.g. nitrogen, oxygen or sulphur. Examples of the cyclic group

include pyrrolidine, imidazoline, piperidine, morpholine, thiomorpholine and piperazine which may be substituted by another unsaturated carboxylic acid group.

$R_1$ and $R_2$ are preferably hydrogen while $R_3$, $R_4$ and $R_6$, which may be the same or different, are preferably hydrogen, an aliphatic radical with 1 to 6 C-atoms or an aromatic radical with 6 to 15 C-atoms, and $R_4$ and $R_6$ may additionally together complete a 5 to 8-membered ring containing nitrogen.

The preferred compounds are obtained by reacting maleic acid anhydride with ammonia, methylamine, dimethylamine, dibutylamine, aniline, N-methylaniline, 4,4'-diaminodiphenylmethane, 4,4'-diaminodiphenylether, 2,4-diaminotoluene, 2,6-diaminotoluene, benzylamine, cyclohexylamine, hexamethylenediamine, isophorone diamine, tris-(aminophenyl)-methane, piperidine or morpholine, and then reacting the resulting amido acid with primary amines from the above mentioned series or from the corresponding isocyanates, this reaction optionally being carried out using derivatives such as the acid chloride of the amido acid. The reaction with the diamides is carried out with aliphatic or aromatic compounds which have at least one isocyanate group in the molecule and are optionally substituted by hetero atoms, e.g. $C_1$–$C_{20}$ alkylisocyanates such as ethyl, methyl, butyl, dodecyl or stearyl isocyanate, substituted or unsubstituted $C_5$–$C_{20}$ aromatic monoisocyanates such as phenyl, tolyl, isopropyl or nonyl isocyanate, nitro-, alkoxy-, aroxy-, chloro-, dichloro-, trichloro-, tetrachloro-, pentachloro-, benzyl- or bromophenyl isocyanate, isocyanatobenzoic, -phthalic or -isophthalic acid esters, isocyanatobenzonitrile, or $C_2$–$C_{10}$ cycloaliphatic isocyanates such as allyl, oleyl or cyclohexenylisocyanate.

The isocyanate components used according to the invention may also be aliphatic, cycloaliphatic, araliphatic, aromatic or heterocyclic polyisocyanates, preferably diisocyanates (see Annalen, 562, pages 75-136), for example ethylene diisocyanate, tetramethylene-1,4-diisocyanate, hexamethylene-1,6-diisocyanate, dodecane-1,12-diisocyanate, cyclobutane-1,3-diisocyanate, cyclohexane-1,3- and -1,4-diisocyanate and any mixtures of these isomers; 1-isocyanato-3,3,5-trimethyl-5-isocyanatomethylcyclohexane (Germany Auslegeschrift No. 1,202,785); hexahydrotolylene-2,4-diisocyanate and -2,6-diisocyanate and any mixtures of these isomers; hexahydrophenylene-1,3-diisocyanate and/or -1,4-diisocyanate; perhydrodiphenylmethane-2,4'-diisocyanate and/or -4,4'-diisocyanate; phenylene-1,3-diisocyanate and -1,4-diisocyanate; tolylene-2,4-diisocyanate and -2,6-diisocyanate and any mixtures of these isomers; diphenylmethane-2,4'-diisocyanate and/or 4,4'-diisocyanate; naphthylene-1,5-diisocyanate; triphenyl methane-4,4',4''-triisocyanate; polyphenylpolymethylene polyisocyanates which can be obtained by aniline-formaldehyde condensation followed by phosgenation and which have been described, for example, in British patent specifications Nos. 874,430 and 848,671; perchlorinated aryl polyisocyanates such as those described, for example, in German Auslegeschrift No. 1,157,601; polyisocyanates with carbodiimide groups as described in German patent specification No. 1,092,007; diisocyanates of the kind described in U.S. Pat. No. 3,492,330; polyisocyanates with allophanate groups as described e.g. in British patent specification No. 99,890, in Belgian Pat. No. 761,626 and in published Dutch Pat. Application No. 7102524; polyisocyanates with isocyanurate groups, e.g. as described in German patent specifications Nos. 1,022,789; 1,222,067 and 1,027,394 and in German Offenlegungsschriften Nos. 1,929,034 and 2,004,048; polyisocyanates with urethane groups as described e.g. in Belgian Pat. No. 752,261 or in U.S. Pat. No. 3,394,164; polyisocyanates with acylated urea groups according to German patent specification No. 1,230,778; polyisocyanates with biuret groups as described e.g. in German patent specification No. 1,101,394, in British patent specification No. 889,050 and in French patent specification No. 7,017,514; polyisocyanates prepared by telomerisation reactions as described, for example, in Belgian Pat. No. 723640, polyisocyanates with ester groups, such as those mentioned, for example, in British patent specifications Nos. 956,474 and 1,072,956, in U.S. Pat. No. 3,567,763 and in German patent specification No. 1,231,688; and reaction products of the above mentioned isocyanates with acetals according to German patent specification No. 1,072,358.

The distillation residues obtained from the commercial production of isocyanates and still containing isocyanate groups may also be used, optionally as solutions in one or more of the above mentioned polyisocyanates. Any mixtures of the above mentioned polyisocyanates may also be used.

Particularly suitable mono- and polyiso(thio)-cyanates are those represented by the following general formulae:

$$R_5(-NCO)_z \text{ or } R_5(-NCS)_z$$

wherein $R_5$ represents an aliphatic group with 1 to 20 C-atoms, an aromatic group with 6 to 12 C-atoms; a cycloaliphatic group with 5 to 12 C-atoms; an aliphatic-aromatic group with 6 to 20 C-atoms; or an aromatic or cycloaliphatic group with 4 to 12 C-atoms containing hetero atoms such as N, O or S. All the radicals may be optionally substituted with halogen, alkyl with $C_1-C_6$ and/or aryl groups with $C_6-C_{16}$.

Aliphatic groups having from 2 to 12 C-atoms and aryl groups having $C_6-C_{16}$ such as phenyl, tolyl, naphthyl, diphenylmethane and diphenylether groups are particularly preferred. z represents an integer of from 1 to 4, preferably 1 to 3 and most preferably 1 or 2.

It is preferred to use commercially readily available mixtures of tolylene diisocyanates, m-phenylenediisocyanate, methyl isocyanate, cyclohexyl isocyanate, phenyl isocyanate and its substitution products, and phosgenated condensates of aniline and formaldehyde having a polyphenylene-methylene structure, the symmetric compounds, 4,4'-diisocyanatodiphenylmethane, 4,4'-diisocyanatodiphenyl ether, p-phenylene diisocyanate and 4,4'-diisocyanatodiphenylmethane, analogous hydroaromatic diisocyanates, and aliphatic diisocyanates with 2 to 12 C-atoms such as hexamethylene diisocyanate and diisocyanate derived from isophorone.

The isocyanates may be used in the free form or they may be used partly or completely in the form of their derivatives which can be obtained by reacting them with compounds containing reactive hydrogen atoms and which function as marked isocyanates under the reaction conditions.

The marked isocyanates preferably used are the acyl ureas obtainable from lactams such as caprolactam and the carbamic acid esters obtained from aromatic or aliphatic monohydroxy or polyhydroxy compounds, which may be represented, for example, by the following general formulae:

$$R_5(-NH-\underset{\underset{O}{\|}}{C}-O-A)_z \text{ or}$$

$$\left[ -\underset{\underset{O}{\|}}{C}-NH-R_5-NH-\underset{\underset{O}{\|}}{C}-O-B-O- \right]_n$$

wherein $R_5$ and z have the meaning already indicated, A represents the organic group of a monohydroxy compound, and B represents the organic group of a difunctional or trifunctional hydroxy compound, preferably both A and B, the same or different, an aliphatic group with 1 to 10 C-atoms, a cycloaliphatic group with 5 to 10 C-atoms, an aliphatic-aromatic group with 7 to 20 C-atoms or an aromatic group with 6-12 C-atoms, each of which groups may be substituted by alkyl with $C_1-C_{10}$ and/or aryl groups with $C_6-C_{16}$, and n represents an integer of from 1 to 1000, preferably from 1 to 100.

Examples of such compounds include the carbamic acid esters obtained from phenol, isomeric cresols, commercial mixtures thereof and similar aromatic hydroxy compounds, aliphatic monohydric alcohols such as methanol, ethanol, propanol, isopropanol, butanol, isobutanol, diethylene glycol monomethyl ether, cyclohexanol, benzyl alcohol and aliphatic diols or polyols such as ethylene glycol or trimethylolpropane.

The urethanes may be put into the process as such or prepared in situ by reaction with alcohols.

Instead of the isocyanates or polyisocyanates mentioned above, the analogous isothiocyanates or polyisothiocyanates may be used.

The reaction according to the invention may be represented by the following reaction scheme:

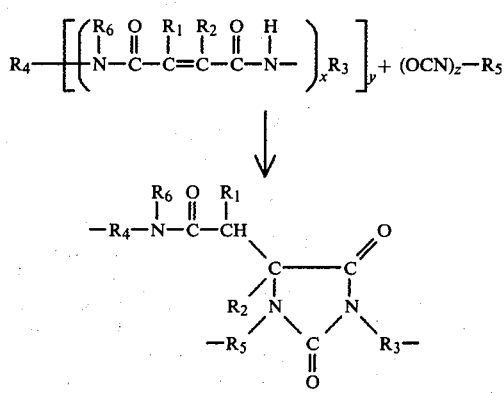

wherein the groups
$R_1$–$R_6$ and x,y,z have the meaning already indicated and the reaction product is a monomolecular compound when x, y and z=1. When x and/or y and/or z>1, the reaction products are oligomeric or higher molecular weight hydantoins in which the hydantoin rings are linked through the groups $R_3$ and/or $R_4$ and/or $R_5$ as indicated by the following recurring structural units:

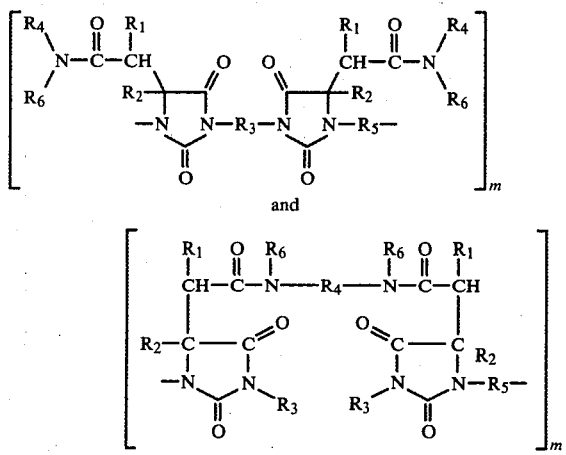

in which $R_1$ to $R_6$ have the meanings already indicated and m represents an integer of from 2 to 1000, preferably from 2 to 100.

The hydantoins prepared according to the invention can be uniquely identified by their IR spectra, in which the characteristic bands for hydantoins and amides occur. The higher molecular weight hydantoins have a solution viscosity of from 250 to 300,000 mPa s, preferably from 1000 to 50,000, as determined on a 30% by weight solution in butyrolactone at 25° C.

The reaction according to the invention may be carried out in solvents which do not react under the reaction conditions or only form addition compounds which are easily split up again, or it may be carried out in an excess of one of the reactants. The following are suitable solvents: (halogenated) hydrocarbons, phenols, esters, lactones, ketones, ethers, substituted amides, nitriles, phosphoric acid amides, sulphoxides and sulphones; for example, xylenes, o-dichlorobenzene, phenol, cresols, benzoic acid alkyl esters, butyrolactone, caprolactone, acetophenone, cyclohexanone, glycol monomethyl ether acetate, diethylene glycol monoethyl ether, dimethylformamide, N-methylpyrrolidone, caprolactam, benzonitrile, hexamethylphosphoric acid triamide, dimethylsulphoxide, tetramethylene sulphone and mixtures thereof. Preferred solvent, are butyrolactone. To carry out the process according to the invention, the reactants, with or without solvent, are kept at temperatures of about 0° to 450° C., preferably from 50° to 250° C., for a length of time which may vary from a few minutes to several hours. The progress of the reaction can be followed by observing the IR spectra and, in the case of higher molecular weight hydantoins, by observing the rise in viscosity. It is in some cases advantageous to carry out the reaction in several stages or to add the individual components in a different sequence or at various temperatures. Especially when preparing polymers, a condensation product may first be prepared, e.g. in a solvent, and this condensation product may then be converted into the high molecular weight reaction product, for example a lacquer film, by a reaction at elevated temperatures with cross-linking or chain lengthening and optionally evaporation of the solvent. If the products are to be used in lacquers, the lacquers may be applied as solvent-free melts or as aqueous dispersions.

The quantity of isocyanate used is generally equivalent to each equivalent of the unsaturated diamide, although it may vary widely from these proportions. Isocyanates and diamides which are monofunctional in the reaction according to the invention give rise to monomolecular hydantoins. Monofunctional diamides and diisocyanates give rise to higher molecular weight polyhydantoins. Polyfunctional diamides and polyfunctional isocyanates give rise to cross-linked hydantoins or hydanoin isocyanates, depending on the stoichiometric proportions of the diamides and isocyanates.

In another embodiment of the invention, the preparation of polyhydantoins according to the invention is carried out in the presence of, for example, polycarboxylic acid anhydrides, polycarboxylic acids and optionally polyols, so that amide, imide and/or ester groups are built into the reaction products. For example, dimethylterephthalate may be condensed with ethylene glycol, glycerol and tris-hydroxyethyl-isocyanurate to produce a polyester, or trimellitic acid anhydride may be condensed with excess diisocyanate to produce a polyamidoimide. The proportions in which these additives are introduced may vary within wide limits but are preferably between 10 and 400% by weight, based on the condensate according to the invention.

The reaction according to the invention may be accelerated by catalysts, e.g. by amines such as triethylamine, 1,4-diazabicyclo-(2,2,2)-octane, N-ethyl-morpholine or N-methyl-imidazole or by organic or inorganic metal compounds, in particular compounds or iron, lead, zinc, tin, copper, cobalt or titanium, e.g. iron(III) chloride, cobalt acetate, lead oxide, lead acetate, zinc octoate, dibutyl tin dilaurate, copper-acetyl acetonate and titanium tetrabutylate, or phosphorus compounds such as trialkylphosphine and 1-methylpholine oxide.

The monomolecular hydantoins which can be prepared by the process according to the invention have pharmaceutical and plant protective activity. They may be also used to improve the flowing properties of lacquers.

The polyhydantoins according to the invention are distinguished by their exceptional temperature resistance and they are suitable for use as adhesives, lacquers, foils and moulded products. Their properties can be varied within wide ranges for various fields of application by adding fillers, pigments and low molecular weight or high molecular weight components, e.g. they may be mixed with polyesters and polycarbamic aced esters for the manufacture of lacquers and foils.

EXAMPLE 1

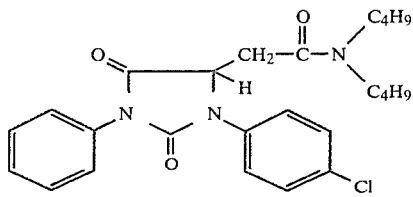

151 g of N,N-dibutyl-N'-phenyl-maleic acid diamide and 77 g of 4-chlorophenyl isocyanate are introduced into 225 g of butyrolactone and heated to 75° C. for one hour, to 100° C. for 2 hours, to 125° C. for 2 hours, to 150° C. for 2 hours and to 170° C. for one hour. 161 g of 1-phenyl-3-(4-chlorophenyl)-4-(N,N-dibutyl-aminocarbonylmethyl)-hydantoin crystallise on cooling and are suction filtered. A further 60 g of hydantoin are precipitated from the filtrate by the addition of water. The combined filter residues are recrystallised from isopropanol and the pure hydantoin is obtained in the form of pale beige polyesters melting at 104° to 105° C. The IR spectrum shows the typical bands of hydantoins at 1715 and 1780 cm$^{-1}$, and a band indicating an amide at 1650 cm$^{-1}$.

$C_{25}H_{30}ClN_3O_3$ (455.5)

|  | C | H | N |
|---|---|---|---|
| Calculated | 65.9 | 6.6 | 9.2% |
| Found | 66.0 | 6.7 | 9.1% |

EXAMPLE 2

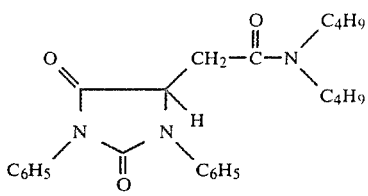

151 g of N,N-dibutyl-N'-phenyl-maleic acid diamide are suspended in 210 g of xylene. 60 g of phenyl isocyanate are then added dropwise at room temperature. The mixture is stirred at 50° C. for one hour, 100° C. for one hour and under mild reflux for 6 hours. The xylene is then distilled from the reaction medium in a thin layer evaporator at 130° C., using a water jet vacuum. 1,3-Diphenyl-4-(N,N'-dibutylaminocarbonylmethyl)-hydantoin is obtained as a brown oil. Its IR spectrum contains the characteristic bands for hydantoin amides at 1715, 1780 and 1650 cm$^{-1}$.

$C_{25}H_{31}N_3O_3$ (421)

| | $C_{25}H_{31}N_3O_3$ (421) | | |
|---|---|---|---|
| | C | H | N |
| Calculated | 71.3 | 7.4 | 10.0% |
| Found | 71.9 | 7.4 | 10.1% |

EXAMPLE 3

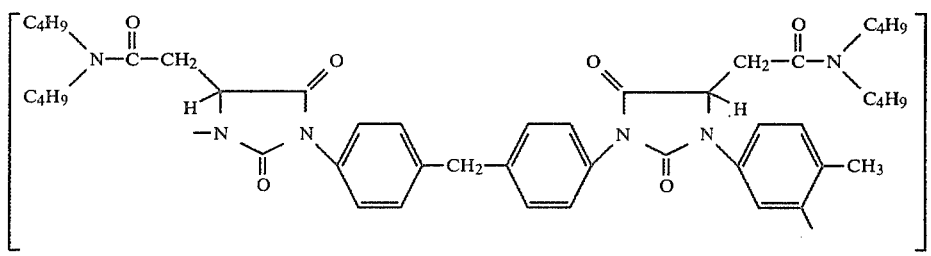

70 g of tolylene-(2,4)-diisocyanate are introduced dropwise at 100° C. into a solution of 247 g of 4,4'-bis-[N,N-dibutyl-maleic acid-diamido-(N')]-diphenylmethane in 475 g of butyrolactone. The reaction mixture is then stirred for 2 hours at 100° C., for 4 hours at 125° C., and for 2 hours at 135° C. The polyhydantoin having the recurrent structural unit indicated above is obtained as a brown solution with a viscosity $\eta^{25}$ of 280 mPa s. The IR spectrum shows the characteristic bands for hydantoins at 1775 cm$^{-1}$, on which the carbonyl band of the solvent is superimposed, and at 1720 cm$^{-1}$ and the characteristic band for amides at 1640 cm$^{-1}$.

A sample of the polyhydantoin solution is painted on a metal sheet and stoved, first at 200° C. and then at 300° C., to form a clear, hard lacquer film.

Another sample is mixed with 40 g of a polyester of terephthalic acid, ethylene glycol and glycerol and 60 g of a commericial cresol mixture, based on 100 g of the solution. The lacquer solution obtained in this way is painted on a glass plate and forms a clear, elastic lacquer film when stoved first at 200° C. and then at 300° C.

EXAMPLE 4

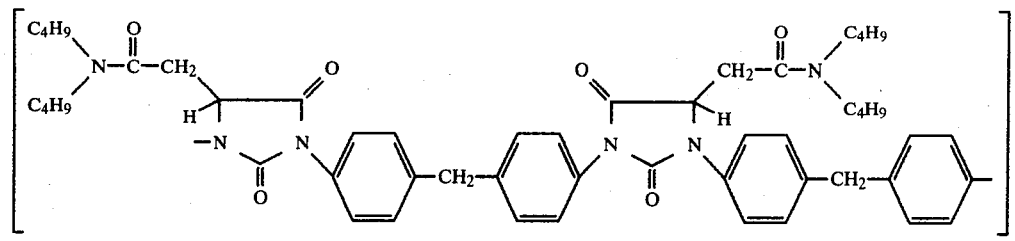

308 g of 4,4'-bis-[N,N-dibutyl-maleic acid diamido-(N')]-diphenylmethane are dissolved in 635 g of butyrolactone at 100° C. 125 g of 4,4'-diisocyanato-diphenylmethane are then introduced and the solution is stirred for 2 hours at 100° C., for 6 hours at 125° C. and for 1 hour at 135° C. A polyhydantoin having the recurrent structural units indicated above is obtained as a brown, viscous approximately 40% solution which has a viscosity $\eta^{25}$ of 3600 mPa s after it has been diluted to a 30% solution with 355 g of butyrolactone. The IR spectrum contains a characteristic band for hydantoins at 1720 cm$^{-1}$ and a characteristic band for amides at 1640 cm$^{-1}$, but the carbonyl band of the solvent is superimposed on the second hydantoin band at 1775 cm$^{-1}$.

A sample of the polyhydantoin solution is painted on a glass plate and stoved, first at 200° C. and then at 300° C., to form a clear, elastic lacquer film.

We claim:

1. A process for the preparation of a hydantoin comprising reacting at a temperature of from 0° to 450° C. an organic monoisocyanate or monoisothiocyanate of the formula $R_5$-NCO or $R_5$-NCS with an unsaturated diamide of the formula:

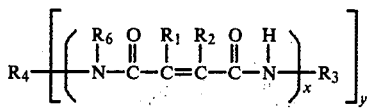

wherein $R_1$, $R_2$, $R_3$, $R_4$ and $R_6$ may be the same or different and each is selected from the group consisting of hydrogen, alkyl of 1–20 carbon atoms, aryl of 6–20 carbon atoms and aralkyl of 7–20 carbon atoms; $R_3$ and $R_4$ are also bivalent and trivalent organic moieties corresponding to the previously mentioned monovalent organic moieties; when x and y are both one, $R_4$ and $R_6$ are additionally together forming a heterocyclic having 3–7 carbon atoms wherein a nitrogen heteroatom is bonded to both $R_4$ and $R_6$; $R_1$ and $R_2$ are also halogen; $R_5$ is selected from the group consisting of unsubstituted or substituted alkyl of 1–20 carbon atoms, unsubstituted or substituted cycloalkyl of 5–12 carbon atoms, unsubstituted or substituted aryl of 6–12 carbon atoms, heterocyclic aryl of 4–12 carbon atoms wherein the hetero atom is N, O or S and heterocycloalkyl of 4–12 carbon atoms wherein the hetero atom is N, O or S, and the substituents are selected from the group consisting of halogen, alkyl of 1–6 carbon atoms and aryl of 6–16 carbon atoms; and x and y each are integers from 1 to 3, with the proviso that at least one of x and y is 1.

2. A process as claimed in claim 1, wherein x and y are integers of 1 or 2.

3. A process as claimed in claim 1, wherein the reaction temperature is from 50° to 250° C.

4. The hydantoin obtained by the process as claimed in claim 1.

* * * * *